United States Patent [19]
Borrod et al.

[11] Patent Number: 4,886,542
[45] Date of Patent: Dec. 12, 1989

[54] HERBICIDE COMPOSITIONS OF N-(PHOSPHONOMETHYLGLYCYL) SULFONYLAMINES AND PROCESS FOR USING SAME

[75] Inventors: Guy Borrod; Guy Lacroix, both of Lyons, France

[73] Assignee: Rhone-Poulenc Agrochimie, Lyons, France

[21] Appl. No.: 35,176

[22] Filed: Apr. 7, 1987

Related U.S. Application Data

[62] Division of Ser. No. 818,722, Jan. 14, 1986, Pat. No. 4,675,429.

[30] Foreign Application Priority Data

Jan. 14, 1985 [FR] France .............................. 85 00619

[51] Int. Cl.$^4$ ............................................. A01N 57/02
[52] U.S. Cl. ..................................... 71/087; 558/145; 558/174
[58] Field of Search ............................................. 71/87

[56] References Cited

U.S. PATENT DOCUMENTS

| | | | |
|---|---|---|---|
| 3,316,331 | 4/1967 | Sims | 558/131 |
| 3,910,969 | 10/1975 | Franz | 71/87 |
| 4,076,690 | 2/1978 | Rosenberger | 558/131 |
| 4,738,708 | 7/1988 | Borrod et al. | 71/81 |

FOREIGN PATENT DOCUMENTS

| | | | |
|---|---|---|---|
| 189358 | 7/1986 | European Pat. Off. | 71/87 |
| 2501185 | 7/1976 | Fed. Rep. of Germany | 558/131 |

OTHER PUBLICATIONS

McOmie, "Protective Groups in Organic Chemistry", (1984), pp. 62–63.

Primary Examiner—Anton H. Sutto
Attorney, Agent, or Firm—Morgan & Finnegan

[57] ABSTRACT

Herbicidal compounds of formula:

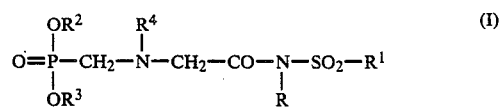

in which
R$^1$ denotes an optionally halogenated alkyl radical containing from 1 to 4 carbon atoms,
R denotes the hydrogen atom or an alkyl group containing from 1 to 4 carbon atoms,
R$^2$ denotes the hydrogen atom or R$^{21}$,
R$^{21}$ and R$^3$ denotes optionally substituted aryl radicals,
R$^4$ denotes a hydrogen atom or a hydrogenolysable group R$^8$, and the agriculturally acceptable salts of these compounds.

10 Claims, No Drawings

HERBICIDE COMPOSITIONS OF N-(PHOSPHONOMETHYLGLYCYL) SULFONYLAMINES AND PROCESS FOR USING SAME

This is a divisional of co-pending application Ser. No. 06/818,722 filed January 14, 1986, now 4,675,429.

The present invention relates to new herbicides from the chemical group of N-(phosphonomethylglycyl)-sulphonylamines, and intermediate products for the preparation of these herbicides, processes for the preparation of these various products, and the application of the said herbicides in agriculture.

Numerous products containing an aminomethylphosphonic group and having herbicidal properties are known, particularly in French Pat. Nos. 2,129,327, 2,281,375, 2,251,569, 2,413,398, 2,463,149, European Pat. Nos. 53,871, 54,382, 73,574, U.S. Pat. Nos. 3,160,632, 3,455,675, 3,868,407, 4,388,103, 4,397,676, British Pat. No. 2,090,596, World Patent WO 83/03,608, and Belgian Pat. Nos. 894,244, 894,245, 894,590, 894,591, 894,592, 894,593, 894,594, 894,595.

Numerous products which are intermediates in the preparation of such products are also known, particularly in European Pat. Nos. 81,459, 97,522, 55,695, French Pat. No. 2,193,830 and U.S. Pat. Nos. 3,835,000 and 4,422,982.

However, it is always desirable to extend the field of available herbicides, in order to respond better to all the needs of the agriculturists, as well as the field of intermediate products which make it possible to produce these, in order to have new synthetic routes available. Indeed, some amides containing an aminomethylphosphonic group were known, but these products were either weakly active or inactive.

An aim of the present invention is, furthermore, to provide herbicides exhibiting high and fast activity.

Another aim of the present invention is to provide herbicides with low persistence and which are readily biodegradable.

Another aim of the present invention is to provide post-emergence herbicides, with a wide activity spectrum, descending systemic action, and which are optionally selective for some crops.

Another aim of the invention is to provide herbicides which have the abovementioned qualities and additionally have pre-emergence activity.

Another aim of the invention is to provide intermediate products and processes permitting access to the herbicides containing an aminomethylphosphonic group.

Another aim of the invention is to provide a very simple and improved process for the preparation of herbicides employing simple reactants, particularly glycine and its simple derivatives.

Other aims and benefits of the invention will become apparent from the description which follows.

It has now been found that these aims could be attained, partly or wholly, by virtue of the compounds according to the invention.

The compounds according to the invention, which can be employed especially either as herbicides or as chemical intermediates, are products of formula:

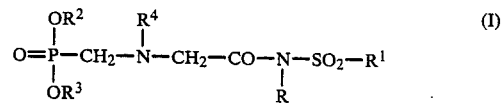

in which:

$R^1$ denotes an alkyl radical, optionally halogenated (preferably chlorinated or fluorinated), containing 1 to 4 carbon atoms, preferably the methyl group, R denotes an alkyl group containing from 1 to 4 carbon atoms, preferably the methyl group, $R^2$ denotes the hydrogen atom or $R^{21}$, $R^{21}$ and $R^3$, which may be identical of different, denote aryl, preferably phenyl, radicals, optionally substituted by one to three substituents such as halogen atoms, alkyl, haloalkyl, alkoxy, cyano, alkylthio, aryloxy, arylthio, or alkoxycarbonyl groups (these various alkyl groups advantageously containing from 1 to 4 carbon atoms, preferably 1 to 2), $R^4$ denotes a hydrogen atom or a hydrogenolysable group $R^8$; in particular $R^8$ can be a radical of formula $Ar(R^5)(R^6)C$- in which Ar is an aromatic group, preferably phenyl, and $R^5$ and $R^6$ are the hydrogen atom or an Ar radical or an alkyl group containing, preferably, 6 carbon atoms at most, and the salts of these various products (especially the salts of the P-OH group and those of the nitrogen atom bearing $R^8$, which then becomes an ammonium group) and particularly the agriculturally acceptable salts of these products. The agriculturally acceptable salts include salts of alkali metals, particularly sodium and potassium, alkaline-earth metal salts, primary, secondary, tertiary or quaternary ammonium salts, and sulphonium salts. Other salts of the invention are salts of addition with an acid such as chlorides, sulphates, phosphates and other salts derived from acids which have a pK lower than or equal to 2.5.

Among the various products according to the invention, a subgroup which is of particular interest owing to the herbicidal activity of the products of which it is formed, comprises the products of formula (I), in the formula of which $R^4$ is the hydrogen atom and more specifically in the formula which $R^3$ is an optionally substituted phenyl radical, preferably unsubstituted phenyl radical $R^4$ is the hydrogen atom.

Furthermore, the products in which $R^2$ is the hydrogen atom form a subgroup which is of great interest because of its high degree of post-emergence activity while the products in which $R^2$ is aryl forms a subgroup which is of more particular interest owing to its pre-emergence activity combined with post-emergence activity.

In the various formula (I), Ar denotes an aromatic group, preferably aryl and more especially phenyl; this radical Ar may, if this is desirable, bear one or more substituents which do not interfere with the reactions involved in the process (for example the substituents alkyl, alkoxy, nitro, halogens and others, the number of carbon atoms being preferably equal to 6 at most), although there appears to be no special advantage in using such substituents.

As $R^8$ radicals mention may be made of the benzyl, 1-phenylethyl, 1-phenylpropyl, naphthylmethyl, 1-naphthylethyl, 1-naphthylpropyl, diphenylmethyl, and trityl (=triphenylmethyl) radicals.

In the (French) present description the chemical compounds are designated by their French nomenclature, but the numbering of the position of substituents is placed before the name of the substituents in accordance with English nomenclature, and not after this name, as in French nomenclature.

The products of formula (I), in which $R^2$ is $R^{21}$ (other than the hydrogen atom), are prepared most conveniently from products of formula:

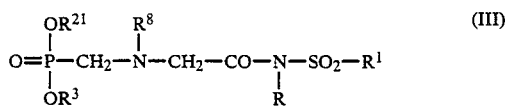

by hydrogenolysis of the group $R^8$. This is a debenzylation in most cases. The operation is advantageously carried out in a liquid, aqueous or organic medium at ambient or elevated temperature, at atmospheric pressure or above. The usual catalysts of hydrogenolysis of the $R^8$ radicals in question can be employed as a catalyst. Water, alcohols such as ethanol or ispropanol, ethers such as tetrahydrofuran and ketones such as acetone or methyl isobutyl ketone (when Pd is used as a catalyst) may be mentioned as a solvent which can be used in helping to make the medium liquid. Palladium, platinum and Raney nickel may be mentioned as suitable catalysts. This catalyst can be employed with or without an inert substrate. It is also possible to use the abovementioned metals, especially palladium and platinum, in the form of salts, hydroxides, or oxides, which are converted to the corresponding metal by the action of hydrogen. As a preferred debenzylation catalyst, use is made of palladium-based catalysts such as palladium on charcoal or palladium on barium sulphate, or palladium hydroxide on charcoal. When the reaction is finished; the catalyst may be separated by filtration and the filtrate may be evaporated; the product of formula (III) is thus obtained practically pure.

A convenient process for the preparation of products of formula (III) consists in reacting a sulphonamide of formula $R-NH-SO_2-R^1$ with a mixed anhydride of formula:

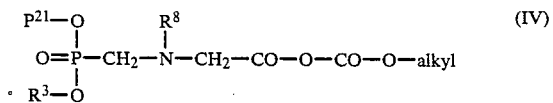

itself obtained by reaction of a product of formula:

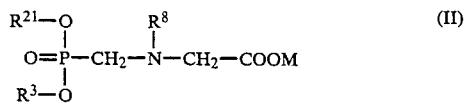

(preferably in salt form) with an alkyl chloroformate (Cl-CO-O-alkyl; alkyl preferably contains 1 to 4 carbon atoms). The product of formula (II) is advantageously employed in the form of an ammonium salt and especially in the form of a salt of a tertiary amine such as triethylamine. The reaction is advantageously carried out at a temperature of between $-30°$ and $+10°$ C. in the presence of solvent; when use is made of a solvent in which the salts formed during the reaction are insoluble, it then suffices to separate the reaction product by filtration. Ethers and esters, especially tetrahydrofuran and ethyl acetate can thus be employed as solvents.

The reaction of the mixed anhydride of formula (IV) with the sulphonamide $R^1-SO_2-NH-R$ is advantageously carried out in a water/organic solvent two-phase medium in the presence of an alkaline agent and a phase transfer catalyst. The temperature is generally between $0°$ and $50°$ C. As phase transfer catalysts (generally employed in a proportion of 0.1 to 10% by weight relative to the mixed anhydride) mention can be made of quaternary ammonium salts of a strong acid, such as tetraalkylammonium or trialkyl aralkylammonium halides or sulphates. An alkali metal hydroxide or carbonate or an alkaline-earth or ammonium hydroxide or carbonate, preferably an alkali metal hydroxide, is advantageously used as an alkaline agent. A water-immiscible organic solvent, for example $CH_2Cl_2$, is used as an organic solvent.

The products of formula (II) are conveniently prepared by the reaction of a phosphite (or phosphonic ester) of formula:

($R^{21}$ and $R^3$ having the same meaning as in formula (I)) with formaldehyde and an N-substituted glycine derivative, the substituent on the nitrogen atom being a hydrogenolysable substituent; this N-substituted glycine derivative is, in practice, a compound of formula $R^8-NH-CH_2-CO-OH$, $R^8$ having the same meaning as previously.

The reaction is generally carried out between 0° and 100° C., preferably between 20° and 90° C. by simply mixing the reactants. Although a large excess (3/1 to ⅓, in molar ratios) of one of the reactants relative to another is possible, in practice it is more advantageous to remain as close as possible to stoichiometry and not to stray by more than 20 mole % from this stoichiometry.

Formaldehyde is employed in any of the conveniently accessible forms. According to the most widely used method it is employed in the form of aqueous solution.

The reaction may be carried out in the presence of an inert solvent but generally there is no merit in using a solvent other than water, the latter being present in a quantity which is generally between 20 and 90%, preferably between 30 and 65%.

The reaction product is isolated by any means known per se.

The products of formula (I) in which $R^2$ is the hydrogen atom, that is to say the products of formula:

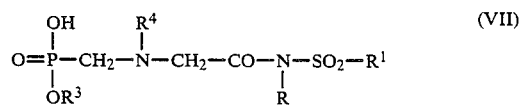

are advantageously prepared by hydrolysis of the products of formula:

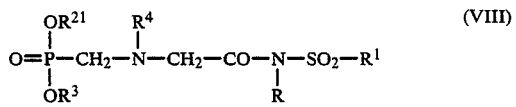

in which R, $R^1$, $R^{21}$, $R^3$, and $R^4$, have the meanings given previously. This hydrolysis is advantageously carried out by simple heating in an acid medium, preferably aqueous (or partially aqueous such as aqueous-alcoholic or water/ketones media), of the product of formula (VIII); the reaction time suitable for replacing $R^{21}$ by H is generally determined by some preliminary measurements of the progress of the reaction under the conditions envisaged at various times. The acid hydrolysis medium is conveniently produced with the aid of strong inorganic or organic acids such as hydrochloric, sulphuric, phosphoric, perchloric or trichloroacetic acids.

The following examples, given without implying a restriction, illustrate the invention and show how it can be employed in practice.

Examples 1 to 4 illustrate the synthesis and the physical properties of herbicidal compounds and chemical intermediates according to the invention.

Example 5 illustrates the post-shoot application of the products according to the invention (the terms post-shoot and post-emergence are synonymous). Example 6 illustrates the pre-shoot application of a product according to the invention (the terms pre-shoot and pre-emergence are synonymous).

In the present description the percentages denote percentages by weight, except for the yields and unless stated otherwise.

By using the procedures of Examples 1 to 4, or similar procedures but varying the reactants, the different compounds Nos. 1 to 48 of general formula (I) were obtained, the individual formulae of which are indicated in Table (II) and the physical characteristics of which are given in Table (III). In table (III) the melting points given may correspond to a phenomenon of melting accompanied by decomposition; where the sign (v) has been inserted, the temperature given is the vitrification point and not the melting point.

Tables (IV) and (V) give the biological results obtained with the compounds of Tables (II) and (III) under the conditions of Examples 5 and 6.

EXAMPLE 1

0.5N aqueous hydrochloric acid (50 cc) and Compound No. 2 (2.26 g) were mixed in a 100 ml reactor. The mixture was refluxed for 15 min and then evaporated to dryness. It was recrystallised with a mixture of acetone and propylene oxide in corresponding proportions of 50/5 by volume. The precipitate was filtered, washed with acetone, and dried. Compound No. 1 (1.4 g) was obtained in the form of a white powder. Yield: 76%.

EXAMPLE 2

In a 250 ml reactor were mixed
tetrahydrofuran (THF) (50 cc)
Compound No. 3 (5 g)
a catalyst (1.7 g) containing 50% of water and 5% of palladium deposited on active charcoal.

Stirring was applied for 40 min under a hydrogen atmosphere and at ambient temperature. The product was filtered, evaporated down and recrystallised from isopropanol. Compound No. 2 (3.2 g) was obtained in the form of a white powder. Yield: 77.7%.

The starting reactant (Compound No. 3) had been prepared in the following manner:

In a 250 ml reactor were mixed
Compound No. 4 (33 g)
THF (70 cc)
triethylamine (8.1 g).

Ethyl chloroformate (8.7 g) was added dropwise at $-10°$ C. and stirring was continued for 1 h 30 min. The precipitate of triethylamine hydrochloride was removed by filtration. The filtrate was evaporated to dryness under vacuum at 30° C. A reddish oil (mixed anhydride) (39.4 g) was obtained.

This oil was mixed with $CH_2Cl_2$ (70 cc) methane-sulphonamide (9.6 g) of formula $CH_3-NH-SO_2-CH_3$, and triethylbenzylammonium chloride (0.4 g). An aqueous solution (6.8 g) of sodium hydroxide (0.085 mole of NaOH) was added dropwise with stirring at 10° C. and stirring was continued for 2 h 30 min. Water (50 cc) was added and separated, the organic phase was washed with water and was then dried and evaporated. After recrystallisation from isopropanol, Compound No. 3 (19 g) was obtained in the form of a white powder. Yield: 47.3%.

EXAMPLE 3

The starting reactant (Compound No. 4) of Example 2 was prepared in the following manner: N-Benzylglycine (39 g), water (80 cc) and an aqueous solution (20.3 cc) of formaldehyde (0.248 mole) were mixed. Diphenyl phosphite $(C_6H_5O)_2PH(O)$ (58 g; 0.248 mole) was added dropwise at ambient temperature. After 30 min the temperature was allowed to rise to 30° C. and stirring was continued for another hour. The product was filtered, washed with water and dried. After recrystallisation from a mixture of isopropyl ether and isopropanol in a proportion of 10/1 by volume, Compound No. 4 (57.4 g) was obtained in the form of a white powder melting at 91° C. Yield: 59.1%.

EXAMPLE 4

To a mixture of Compound No. 28 (9 g) in acetone (80 cc) was added 3N aqueous hydrochloric acid (6 cc). The mixture was heated for 2 hours at boiling point under reflux. It was cooled and propylene oxide (5 cc) was added. The precipitate was filtered and the filtrate was washed in acetone and dried. Compound No. 16 (3 g) (yield 43%) was thereby obtained.

EXAMPLE 5

Post-Emergence Herbicidal Application to Plant Species

A number of seeds determined as a function of the plant species and of the size of the seed were sown in $9 \times 9 \times 9$ cm pots filled with light agricultural soil.

The seeds were then covered with a soil layer approximately 3 mm thick and the seeds were allowed to germinate until it produces a plantlet at a suitable stage. The treatment stage for graminaceous plants is the "second leaf developing" stage. In the case of dicotyledon plants, the treatment stage is the "developed cotyledon leaves, first true leaf developing" stage.

The pots were then sprayed with the spraying mixture in a quantity corresponding to a volume application rate of 500 l/ha, the spraying mixture containing the active ingredient in the required concentration.

The spraying mixture employed for the treatment was an aqueous suspension or solution of the active ingredient containing Cemulsol NP 10 (a surface-active agent consisting of a polycondensate of ethylene oxide with an alkylphenol, particularly nonylphenol) (0.1% by weight) and Tween 20 (a surface-active agent consisting of an oleate of an ethylene oxide polycondensate derivative of sorbitol) (0.04% by weight).

Depending on the concentration of the active ingredient in the spraying mixture, the active ingredient was applied at rates of 1 and 4 kg/ha.

The treated pots were then placed in troughs intended to receive the moistening water, by sub-irrigation, and were kept for 28 days at ambient temperature under 70% relative humidity.

After 28 days, the number of living plants in the pots treated with the spraying mixture containing the active ingredient to be tested and the number of living plants in a control pot treated under the same conditions but with a spraying mixture not containing active ingredient were counted. In this way, the percentage destruction of the treated plants was determined relative to the untreated control. A percentage destruction of 100% indicates that there has been complete destruction of the plant species in question and a percentage of 0% indicates that the number of living plants in the treated pots was identical to that in the control pot.

The plants employed in the tests were:

TABLE (I)

| Abbreviations | Name | Latin name |
| --- | --- | --- |
| AVF | wild oat | Avena fatua |
| ECH | panic grass | Echinochloa crus-galli |
| LOL | ray grass | Lolium multiflorum |
| PHS | French bean | Phaseolus vulgaris |
| SIN | white mustard | Sinapis alba |
| CHE | goosefoot | Chenopodium album |
| CYP | cyperus | Cyperus esculentus |
| IPO | ipomea | Ipomea purpurea |
| CEN | blueberry | Centaurea cyanus |
| ABU | abutilon | Abutilon theophrasti |
| DAU | wild carrot | Daucus carota |

The results obtained are shown in Table (IV):

EXAMPLE 6

Pre-Emergence Herbicidal Application to Plant Species

A number of seeds which was determined as a function of the plant species and of the size of the seed were sown in 9×9×9 cm pots filled with light agricultural soil.

The pots were sprayed with spraying mixture in a quantity corresponding to a volume application rate of 500 l/ha, the mixture containing the active ingredient at the required concentration.

The treatment with the spraying mixture was thus carried out on seeds which were not covered with soil (the term spraying mixture is employed to denote, generally, the water-diluted compositions as they are applied to the plants).

The spraying mixture employed for the treatment was prepared as in Example 5.

The rate of application of active ingredient was 4 kg/ha.

After treatment the seeds were covered with a soil layer approximately 3 mm thick.

The pots are then placed in troughs intended to receive the moistening water, by sub-irrigation, and kept for 28 days at ambient temperature under 70% relative humidity.

After 28 days the herbicidal effects were observed and evaluated in the same way as in Example 5. The results obtained in this Example 6 are shown in Table (V).

The tests carried out show, consequently, the remarkably advantageous properties of the compounds according to the invention, as herbicides with a wide activity spectrum and active in post-emergence (particularly in the case of the compounds of formula (I) in which $R^2$ is the hydrogen atom) and also in pre-emergence (particularly in the case of compounds of formula (I) wherein ($R^{21}$) $R^2/$ is aryl).

For their use in practice, the compounds according to the invention are rarely employed by themselves. Most frequently, these compounds form part of formulations. These formulations, which can be employed as herbicidal agents, contain, as active ingredient, a compound according to the invention such as described previously in combination with solid or liquid carriers which are agriculturally acceptable and surface-active agents which are also agriculturally acceptable. In particular, the usual inert carriers and the usual surface-active agents may be employed. These formulations are also part of the invention.

These formulations can also contain all kinds of other ingredients such as, for example, protective colloids, adhesives, thickeners, thixotropic agents, penetrating agents, stabilisers, sequestering agents, and the like, as well as other known active substances with pesticidal properties (particularly insecticides, fungicides or herbicides) or with plant growth regulating properties. More generally, the compounds employed in the invention may be combined with all the solid or liquid additives corresponding to the usual formulating techniques.

The use dosages of the compounds employed in the invention may vary within wide limits, particularly depending on the nature of the adventitious plants to be eliminated and the usual degree of infestation of the crops with these adventitious plants.

In general, the formulations according to the invention usually contain from 0.05 to 95%, approximately, (by weight) of one or more active substances according to the invention, from 1% to 95%, approximately, of one or more solid or liquid carriers and optionally from 0.1 to 50%, approximately, of one or more surface-active agents.

In accordance with what has already been stated the compounds employed in the invention are generally combined with carriers and optionally surface-active agents.

In the present description, the term "carrier" denotes an organic or inorganic, natural or synthetic substance with which the active ingredient is combined to facilitate its application to the plant, to the seeds or to the soil. This carrier is thus generally inert and it must be agriculturally acceptable, particularly on the plant treated. The carrier may be solid (clays, natural or synthetic silicates, silica, resins, waxes, solid fertilisers, and the like) or liquid (water; alcohols, particularly butanol; esters, particularly methyl-glycol acetate; ketones, particularly cyclohexanone and isophorone; petroleum fractions; aromatic hydrocarbons, particularly the xylenes, or paraffinic hydrocarbons; chlorinated aliphatic hydrocarbons, particularly trichloroethane, or chlorinated aromatic hydrocarbons, particularly the chlorobenzenes; water-soluble solvents such as dimethylformamide, dimethyl sulphoxide, or N-methylpyrrolidone; liquefied gases, and the like).

The surface-active agent may be an emulsifying agent, dispersing agent or wetting agent of an ionic or nonionic type or a mixture of such surface-active agents. Mention may be made, for example, of salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (particularly alkylphenols or arylphenols), salts of esters of sulphosuccinic acids, taurine derivatives (particularly alkyltaurates), phosphoric esters of ethylene oxide polycondensates with phenols or alcohols, esters of fatty acids with polyols, and functional sulphate, sulphonate and phosphate derivatives of the above compounds. The presence of at least one surface-active agent is generally essential when the active ingredient and/or the inert carrier are water-insoluble and the vector agent of the application is water.

For their application, the compounds of formula (I) are thus generally in the form of formulations; these formulations according to the invention are themselves in fairly varied, solid or liquid forms.

Solid formulations which can be mentioned are dusting powders (with a content of compound of formula (I) which may go up to 100%) and granulates, particularly those obtained by extrusion, by compacting, by impregnation of a granular carrier, by granulation starting from a powder (the content of compound of formula (I) in these granulates being between 0.5 and 80% in these latter cases).

As liquid formulations or those intended to form liquid formulations when applied, mention can be made of solutions, in particular emulsifiable concentrates, emulsions, flowables, aerosols, wettable powders (or spraying powder), dry flowables and pastes.

The emulsifiable or soluble concentrates also contain 10 to 80% of active ingredient in most cases, while the emulsions or solutions which are ready for application contain 0.01 to 20% of active ingredient. Besides the solvent, the emulsifiable concentrates can contain, when required, 2 to 20% of suitable additives such as stabilisers, surface-active agents, penetrating agents, corrosion inhibitors, colorants or adhesives.

By diluting these concentrates with water it is possible to obtain emulsions of any required concentration, which are especially suitable for application to the plants.

By way of example, formulations of some emulsifiable concentrates were prepared as follows:

EXAMPLE 7

| active ingredient, Compound No. 1 | 250 g |
|---|---|
| polycondensate of ethylene oxide with alkylphenol | 30 g |
| calcium alkylarylsulphonate | 50 g |
| petroleum distillation cut distilling between 160 and 185° C. | 670 g |

EXAMPLE 8

| active ingredient, Compound No. 1 | 350 g |
|---|---|
| polycondensate of ethylene oxide with castor oil | 60 g |
| sodium alkylarylsulphonate | 40 g |
| cyclohexanone | 150 g |
| xylene | 400 g |

EXAMPLE 9

| active ingredient, Compound No. 1 | 400 g |
|---|---|
| polycondensate of ethylene oxide with alkylphenol | 100 g |
| ethylene glycol methyl ether | 250 g |
| aromatic petroleum cut distilling at 160–185° C. | 250 g |

EXAMPLE 10

| active ingredient, Compound No. 1 | 400 g |
|---|---|
| polycondensate of ethylene oxide with tristyrylphenol phosphate | 50 g |
| polycondensate of ethylene oxide with alkylphenol phosphate | 65 g |
| sodium alkylbenzenesulphonate | 35 g |
| cyclohexanone | 300 g |
| aromatic petroleum cut distilling at 160–185° C. | 150 g |

EXAMPLE 11

| active ingredient, Compound No. 1 | 400 g/l |
|---|---|
| alkali metal dodecylbenzenesulphonate | 24 g/l |
| nonylphenol condensate with 10 molecules of ethylene oxide | 16 g/l |
| cyclohexanone | 200 g/l |
| aromatic solvent q.s. | 1 liter. |

EXAMPLE 12

| active ingredient, Compound No. 1 | 250 g |
|---|---|
| epoxidised vegetable oil | 25 g |
| mixture of alkylarylsulphonate, polyglycol ether and fatty alcohols | 100 g |
| dimethylformamide | 50 g |
| xylene | 575 g |

The flowables, which can be applied by spraying, are prepared so as to produce a stable fluid product which does not settle (fine grinding) and usually contain from 10 to 75% of active ingredient, from 0.5 to 15% of surface-active agents, from 0.1 to 10% of thixotropic agents, from 0 to 10% of suitable additives, such as antifoams, corrosion inhibitors, stabilisers, penetrating agents and adhesives and, as carrier, water or an organic liquid in which the active ingredient is poorly soluble or insoluble: certain organic solid substances or inorganic salts may be dissolved in the carrier to help to prevent sedimentation, or as antifreezes for water.

As an example, a formulation of a flowable was prepared as follows:

EXAMPLE 13

| active ingredient, Compound No. 1 | 500 g |
|---|---|
| polycondensate of ethylene oxide with tristyrylphenol phosphate | 50 g |
| polycondensate of ethylene oxide with alkylphenol | 50 g |
| sodium polycarboxylate | 20 g |

-continued

| | |
|---|---|
| ethylene glycol | 50 g |
| organopolysiloxane oil (antifoam) | 1 g |
| polysaccharide | 1.5 g |
| water | 316.5 g |

The wettable powders (or dusting powders) are usually prepared so that they contain 20 to 95% of active ingredient, and they usually contain, in addition to the solid carrier, from 0 to 5% of a wetting agent, from 3 to 10% of a dispersing agent and, when required, from 0 to 10% of one or more stabilisers and/or other additives such as penetrating agents, adhesives, or anti-caking agents, colorants, and the like.

By way of example, various formulations of wettable powders were prepared as follows:

EXAMPLE 14

| | |
|---|---|
| active ingredient, Compound No. 1 | 50% |
| calcium lignosulphonate (deflocculant) | 5% |
| isopropylnaphthalenesulphonate (anionic wetting agent) | 1% |
| anticaking silica | 5% |
| kaolin (filler) | 39% |

EXAMPLE 15

| | |
|---|---|
| active ingredient, Compound No. 1 | 80% |
| sodium alkylnaphthalenesulphonate | 2% |
| sodium lignosulphonate | 2% |
| anticaking silica | 3% |
| kaolin | 13% |

EXAMPLE 16

| | |
|---|---|
| active ingredient, Compound No. 1 | 50% |
| sodium alkylnaphthalenesulphonate | 2% |
| low viscosity methyl cellulose | 2% |
| diatomaceous earth | 46% |

EXAMPLE 17

| | |
|---|---|
| active ingredient, Compound No. 1 | 90% |
| sodium dioctylsulphosuccinate | 0.2% |
| synthetic silica | 9.8% |

EXAMPLE 18

| | |
|---|---|
| active ingredient, Compound No. 1 | 400 g |
| sodium lignosulphonate | 50 g |
| sodium dibutylnaphthalenesulphonate | 10 g |
| silica | 540 g |

EXAMPLE 19

| | |
|---|---|
| active ingredient, Compound No. 1 | 250 g |
| isooctylphenoxy-polyoxyethylene-ethanol | 25 g |
| equal-weight mixture of Champagne chalk and hydroxyethylcellulose | 17 g |
| sodium aluminosilicate | 543 g |
| kieselguhr | 165 g |

EXAMPLE 20

| | |
|---|---|
| active ingredient, Compound No. 1 | 100 g |
| mixed sodium salts of saturated fatty acid sulphates | 30 g |
| formaldehyde/naphthalenesulphonic acid condensate | 50 g |
| kaolin | 820 g |

To produce these sprayable powders or wettable powders, the active ingredients are intimately mixed in suitable mixers with the additional substances, or the molten active ingredient is used to impregnate the porous filler, followed by grinding in mills or other suitable grinders. This produces sprayable powders with advantageous wettability and suspendibility; they can be suspended in water at any required concentration and this suspension can be employed very advantageously especially for application to plant foliage.

The dry flowables (self-dispersible granulates; these are, in fact, granules which are readily dispersible in water) have a composition which is substantially close to that of the wettable powders. They can be prepared by granulation of formulations described for wettable powders, either by a wet route (contacting the finely divided active ingredient with the inert carrier and a little water, for example 1 to 20%, or with aqueous solution of dispersant or binder, followed by drying and screening), or by a dry route (compacting followed by grinding and screening).

As an example, a formulation of a dry flowable was prepared as follows

Example 21

| | |
|---|---|
| active ingredient Compound No. 1 | 800 g |
| sodium alkylnaphthalenesulphonate | 20 g |
| sodium methylenebis(naphthalenesulphonate) | 80 g |
| kaolin | 100 g |

Pastes may be produced instead of wettable powders. The conditions and methods for producing and using these pastes are similar to those for wettable powders or sprayable powders.

As already stated, the aqueous dispersions and emulsions, for example the formulations obtained by diluting with water a wettable powder or an emulsifiable concentrate according to the invention, are included in the general scope of the formulations which can be employed in the present invention. The emulsions may be of the water-in-oil or oil-in-water type and may have a thick consistency such as that of a "mayonnaise".

All these aqueous dispersions or emulsions, or spraying mixtures, can be applied to the crops to be weeded by any suitable means, mainly by spraying, at rates which are usually of the order of 100 to 1200 liters of spraying mixture per hectare.

The granulates which are intended to be scattered on the ground are usually prepared so that they are between 0.1 and 2 mm in size and they can be manufactured by agglomeration or impregnation. Preferably, the granulates contain 1 to 25% of active ingredient and 0 to 10% of additives such as stabilisers, slow-release modifiers, binders and solvents.

According to an example of granulate formulation, the following components were employed

Example 22

| | |
|---|---|
| active ingredient, Compound No. 1 | 50 g |
| propylene glycol | 25 g |
| boiled linseed oil | 50 g |
| clay (particle size: 0.3 to 0.8 mm) | 910 g |

The present invention also relates to a weeding process which consists in applying an effective quantity of a compound of formula (I) to the plants which are to be destroyed.

The products and formulations according to the invention are readily applied to plants and especially to the weeds to be eradicated when the latter have green foliage. Since their persistence is low, the operation can be carried out so that the crop is sown before or after treatment but emerges shortly after treatment (2 to 3 weeks), that is to say after the products of the invention have decomposed.

In the case of compounds suitable for this application, it is also possible to employ a weeding process which consists in applying an effective quantity of a compound of formula (I) to the areas or ground where the intention is to prevent the growth or the development of plants which have not yet grown (pre-emergence application).

The rate of application of active ingredient is usually between 0.1 and 10 kg/ha, preferably between 0.5 and 8 kg/ha (usually 100 to 1200 liters of spraying mixture per hectare).

The main function of the various additives or adjuvants mentioned earlier is generally to facilitate the handling and the scattering of the products according to the invention. In some cases, they can also assist the entry of the active ingredient into the plant and, consequently, can increase the normal activity of the active ingredients according to the invention.

The herbicidal formulations and their application can also be employed shortly before the harvest so as to kill the weeds the roots of which survive in the soil after the harvest. It is thus possible to sow very quickly after the harvest without the need for carrying out mechanical weeding operations (ploughing or other).

TABLE (II)

| | | $R^2 = R^3 = X-C_6H_4-$ | | | $R^3 = X-C_6H_4-$; $R^4 = H$ $R^2 = H$ compound n° |
|---|---|---|---|---|---|
| R | $R^1$ | X and position of-X on $C_6H_4$ | $R^4 = H$ compound n° | $R^4 =$ benzyl compound n° | |
| $CH_3$ | $CH_3$ | 2-$CH_3$ | 26 | 35 | 12 |
| $CH_3$ | $CH_3$ | 3-$CH_3$ | 27 | 36 | 15 |
| $CH_3$ | $CH_3$ | 4-$CH_3$ | 28 | 37 | 16 |
| $CH_3$ | $CH_3$ | 4-$CH_3O$ | 29 | 38 | 17 |
| $CH_3$ | $CH_3$ | 4-t-Bu | 30 | 39 | 18 |
| $CH_3$ | $CH_3$ | 2-$CH_3O$ | | 40 | 13 |
| $CH_3$ | $CH_3$ | 2-Cl | | | 14 |
| $C_2H_5$ | $CH_3$ | H | 19 | 41 | 5 |
| n-$C_3H_7$ | $CH_3$ | H | 20 | 42 | 6 |
| cy-clo-pro-pyl | $CH_3$ | H | 21 | | 7 |
| $CH_3$ | $CH_3CHCl$ | H | 25 | 43 | 11 |
| $CH_3$ | $(CH_3)_2CH$ | H | 22 | 44 | 8 |
| $CH_3$ | $C_3H_7$ | H | 23 | 45 | 9 |
| $CH_3$ | $Cl$-$CH_2$ | H | 24 | 46 | 10 |
| $CH_3$ | $CH_3$ | H | 2 | 3 | 1 |
| $CH_3$ | $(CH_3)_2CH$ | 4-$CH_3$ | 33 | 47 | 31 |
| $C_2H_5$ | $(CH_3)_2CH$ | H | 34 | 48 | 32 |

TABLE (III)

| Compound n° | Melting point in °C. | Refractive index $n_D^{20}$ | Characteristics of NMR spectra. Displacements (delta; d) in ppm or coupling constants (J) in hertz |
|---|---|---|---|
| 1 | 165 | | |
| 2 | 95 | | |
| 3 | 121 | | |
| 4 | 91 | | |
| 5 | 195 | | |
| 6 | 201 | | |
| 7 | 210 | | |
| 8 | 187 | | |
| 9 | 190 | | |
| 10 | 178 | | |
| 11 | 131 | | |
| 12 | 115 (v) | | |
| 13 | 185 | | |
| 14 | 147 | | |
| 15 | 115 (v) | | |
| 16 | 196 | | |
| 17 | 202 | | |
| 18 | 156-159 | | |
| 19 | 83 | | |
| 20 | 64 | | |
| 21 | 93 | | |
| 22 | 83 | | |
| 23 | | 1.545 | |
| 24 | 89 | | |
| 25 | | 1.556 | |
| 26 | | 1.5495 | |
| 27 | | 1.549 | |
| 28 | | 1.548 | |
| 29 | 81 | | |
| 30 | | 1.526 | |
| 31 | 196 | | |
| 32 | 95 (v) | | |
| 33 | | 1.546 | |
| 34 | | 1.543 | |
| 35 | | 1.5565 | |
| 36 | | 1.5605 | |
| 37 | | 1.556 | |
| 38 | 90 | | |
| 39 | | 1.522 | |
| 40 | | 1.555 | |
| 41 | | | d = 3.6, (J = 8.8); 3.96; 4.10 |
| 42 | | | d = 3.58, (J = 9.2); 3.92; 4.10 |
| 43 | | | d = 3.59, (J = 9.2); 3.94; 4.08 |
| 44 | | | d = 3.60, (J = 9.2); 3.94; 4.06 |
| 45 | | 1.526 | d = 3.62, (J = 8.8); 3.92; 4.08 |
| 46 | | | d = 3.58, (J = 9.2); 3.96; 4.08 |
| 47 | | 1.545 | |
| 48 | | | d = 3.70, (J = 9.2); 3.91; 4.10 |
| 49 | | | |
| 50 | | | |

TABLE (IV)

| | | Post-emergence activity (in %) | | | | | |
|---|---|---|---|---|---|---|---|
| Compound | Dose in kg/ha | AVF | ECH | LOL | CYP | CEN | IPO |
| 1 | 4 | 80 | 95 | 100 | 100 | 100 | 100 |
| 1 | 1 | 30 | 95 | 90 | 100 | 100 | 95 |
| 1 | 0.25 | 30 | 95 | 50 | 20 | 50 | 50 |
| 5 | 4 | 40 | 100 | 100 | 100 | 100 | 100 |
| 5 | 1 | 30 | 100 | 100 | 0 | 100 | 80 |
| 6 | 4 | 30 | 100 | 100 | 20 | 100 | 100 |
| 6 | 1 | 30 | 100 | 80 | 20 | 50 | 50 |
| 7 | 1 | 20 | 100 | 80 | 0 | 100 | 20 |
| 8 | 1 | 0 | 95 | 60 | 0 | 100 | 0 |
| 9 | 1 | 0 | 95 | 40 | 0 | 100 | 30 |
| 10 | 1 | 20 | 100 | 40 | 30 | 100 | 90 |
| 11 | 4 | 40 | 100 | 100 | 90 | 100 | 60 |
| 11 | 1 | 20 | 100 | 90 | 90 | 100 | 50 |

TABLE (IV)-continued

| | | Post-emergence activity (in %) | | | | | |
|---|---|---|---|---|---|---|---|
| Compound | Dose in kg/ha | AVF | ECH | LOL | CYP | CEN | IPO |
| 12 | 4 | 50 | 100 | 100 | 95 | 100 | 100 |
| 13 | 4 | 80 | 100 | 100 | 60 | 100 | 95 |
| 13 | 1 | 40 | 100 | 100 | 20 | 100 | 50 |
| 14 | 4 | 80 | 100 | 100 | 40 | 100 | 95 |
| 14 | 1 | 30 | 100 | 95 | 50 | 40 | 100 |
| 15 | 4 | 20 | 100 | 100 | 20 | 100 | 50 |
| 16 | 4 | 20 | 100 | 95 | 80 | 100 | 50 |
| 16 | 1 | 20 | 100 | 80 | 20 | 100 | 80 |
| 17 | 4 | 95 | 100 | 100 | 60 | 100 | 100 |
| 17 | 0.25 | 40 | 100 | 90 | 20 | 100 | 30 |
| 18 | 4 | 30 | 100 | 95 | 50 | 100 | 50 |
| 18 | 1 | 40 | 100 | 98 | 30 | 100 | 30 |
| 2 | 4 | — | 98 | 80 | — | 100 | 90 |
| 2 | 1 | — | 98 | 70 | — | 100 | 50 |
| 19 | 4 | 20 | 100 | 95 | 20 | 100 | 30 |
| 20 | 4 | 20 | 100 | 80 | 0 | 100 | 100 |
| 21 | 4 | 30 | 100 | 90 | 20 | 100 | 30 |

TABLE V

| | | Pre-emergence activity (in %) | | | | | | |
|---|---|---|---|---|---|---|---|---|
| Compound | Dose in kg/ha | ECH | LOL | CEN | IPO | SIN | ABU | PHS |
| 2 | 4 | 20 | 98 | — | — | 98 | — | 100 |
| 19 | 4 | 30 | 98 | 50 | — | 90 | 50 | 70 |
| 25 | 4 | 20 | 20 | 100 | — | 90 | 98 | 50 |

We claim:

1. A weeding process wherein an effective amount of a compound of the formula:

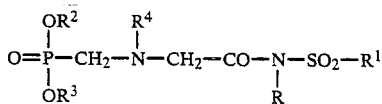

wherein:
R is hydrogen or alkyl having from 1 to 4 carbon atoms;
$R^1$ is alkyl having from 1 to 4 carbon atoms, and substituted with hydrogen or halogen;
$R^2$ is hydrogen or $R^{21}$;
$R^{21}$ is a radical having the same meaning as $R^3$;
$R^3$ is aryl substituted with hydrogen, halogen, alkyl, haloalkyl, alkoxy, cyano, alkylthio, aryloxy, arylthio or alkoxycarbonyl; and
$R^4$ is hydrogen or a hydrogenolysable group, $R^8$; and
$R^8$ is $Ar(R^5)(R^6)C-$ wherein Ar is aryl, each of $R^5$ and $R^6$ is hydrogen, aryl or alkyl, is applied to the foliage of the plants to be eradicated.

2. A pre-emergence weeding process wherein an effective amount of a compound of formula

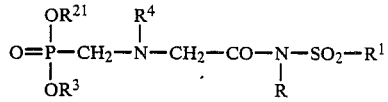

wherein:
R is hydrogen or alkyl having from 1 to 4 carbon atoms;
$R^1$ is alkyl having from 1 to 4 carbon atoms, and substituted with hydrogen or halogen;
$R^3$ is aryl substituted with hydrogen, halogen, alkyl, haloalkyl, alkoxy, cyano, alkylthio, aryloxy, arylthio or alkoxycarbonyl;
$R^4$ is hydrogen or a hydrogenolysable group, $R^8$;
$R^8$ is $Ar(R^5)(R^6)C-$ wherein Ar is aryl, each of $R^5$ and $R^6$ is hydrogen, aryl or alkyl; and
$R^{21}$ is a radical having the same meaning as $R^3$, is applied to the ground.

3. A weeding process according to claims 1 or 2 wherein the compound is applied at a rate of 0.1 to 10 kg/ha.

4. A weeding process according to claim 3 wherein the compound is applied at a rate of 0.5 to 8 kg/ha.

5. A herbicidal composition containing as an active ingredient a compound selected from the group consisting of the formula:

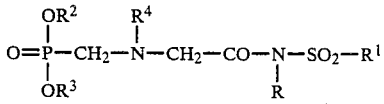

wherein;
R is hydrogen or alkyl having from 1 to 4 carbon atoms;
$R^1$ is alkyl having from 1 to 4 carbon atoms, and substituted with hydrogen or halogen;
$R^2$ is hydrogen or $R^{21}$;
$R^{21}$ is a radical having the same meaning as $R^3$;
$R^3$ is aryl substituted with hydrogen, halogen, alkyl, haloalkyl, alkoxy, cyano, alkylthio, aryloxy, arylthio or alkoxycarbonyl;
$R^4$ is hydrogen or a hydrogenolysable group, $R^8$; and
$R^8$ is $Ar(R^5)(R^6)C-$ wherein Ar is aryl, each of $R^5$ and $R^6$ is hydrogen, aryl or alkyl; an agriculturally acceptable salt thereof and an inert carrier.

6. A herbicidal composition according to claim 5 wherein the active ingredient is about 0.05 to 95% by weight.

7. A herbicidal composition according to claim 5 wherein the active ingredient is about 5 to 50% by weight.

8. A herbicidal composition according to claims 5, 6 or 7 wherein the composition is an emulsifiable concentrate.

9. A composition according to claims 5, 6 or 7 wherein the composition is a soluble powder.

10. A composition according to claims 5, 6, or 7 wherein the composition is a dry flowable.

* * * * *